(12) United States Patent
Richard et al.

(10) Patent No.: US 12,396,928 B2
(45) Date of Patent: Aug. 26, 2025

(54) DELIVERY SYSTEM FOR PROVIDING SELF-HARDENING CALCIUM SILICATE BASED COMPOSITIONS USED IN MEDICAL APPLICATIONS

(71) Applicant: SEPTODONT OU SEPTODONT SAS OU SPECIALITES SEPTODONT, Saint-Maurdes-Fossés (FR)

(72) Inventors: Gilles Richard, Crosne (FR); Julie Guérin, Orsay (FR); Julie Penou, Yerres (FR); Johanna Filin, Saint-Maur-des-Fossés (FR)

(73) Assignee: SEPTODONT OU SEPTODONT SAS OU SPECIALITES SEPTODONT, Saint-Maur-des-Fossés (FR)

( * ) Notice: Subject to any disclaimer, the term of this patent is extended or adjusted under 35 U.S.C. 154(b) by 934 days.

(21) Appl. No.: 17/427,220

(22) PCT Filed: Feb. 28, 2020

(86) PCT No.: PCT/EP2020/055302
§ 371 (c)(1),
(2) Date: Jul. 30, 2021

(87) PCT Pub. No.: WO2020/178179
PCT Pub. Date: Sep. 10, 2020

(65) Prior Publication Data
US 2023/0120448 A1    Apr. 20, 2023

(30) Foreign Application Priority Data
Mar. 1, 2019 (EP) .................... 19305241

(51) Int. Cl.
*A61K 6/853* (2020.01)
*A61K 6/878* (2020.01)
*A61L 24/02* (2006.01)

(52) U.S. Cl.
CPC ............. *A61K 6/853* (2020.01); *A61K 6/878* (2020.01); *A61L 24/02* (2013.01); *A61L 2430/02* (2013.01); *A61L 2430/12* (2013.01)

(58) Field of Classification Search
CPC ......... A61K 6/853; A61K 6/878; A61L 24/02; A61L 2430/02; A61L 2430/12; C04B 2111/00836; C04B 28/04; C04B 40/0625; C04B 40/065; C04B 28/02
See application file for complete search history.

(56) References Cited

U.S. PATENT DOCUMENTS

| | | | |
|---|---|---|---|
| 8,481,065 B2 | 7/2013 | O'Mahony et al. | |
| 8,974,586 B2 * | 3/2015 | Richard | A61K 6/78 106/35 |
| 10,016,257 B2 | 7/2018 | Pauser et al. | |
| 2013/0066324 A1 | 3/2013 | Engqvist et al. | |
| 2015/0183687 A1 | 7/2015 | Engqvist et al. | |
| 2017/0340523 A1 | 11/2017 | Guzman | |

FOREIGN PATENT DOCUMENTS

| | | |
|---|---|---|
| EP | 2 637 628 B1 | 11/2016 |
| EP | 3 111 913 A1 | 1/2017 |
| WO | 2007/047994 A2 | 4/2007 |
| WO | 2008128347 A1 | 10/2008 |
| WO | 2012/065946 A1 | 5/2012 |
| WO | 2013041709 A1 | 3/2013 |

OTHER PUBLICATIONS

Saghiri et al., "Calcium silicate-based cements and functional impacts of various constituents", Dental Materials Journal, Jan. 31, 2017, vol. 36, No. 1, 22 pages.
International Search Report and Written Opinion of the International Searching Authority issued on May 25, 2020 in corresponding International application No. PCT/EP2020/055302; 11 pages.

* cited by examiner

*Primary Examiner* — Anthony J Green
(74) *Attorney, Agent, or Firm* — Maier & Maier, PLLC (57) ABSTRACT

Delivery and/or injection systems, preferably for medical applications. Especially, a kit of parts for providing a dental composition able to self-hardening. The kit of parts includes a first waterproof container including an anhydrous calcium silicate phase; and a second container including an aqueous phase. The kit of parts may be used in delivery and/or injection systems so that it delivers a homogenous calcium silicate-based composition having a volume ratio between the calcium silicate phase and the aqueous phase ranging from 1 to 3. Also, the hardened material obtained from the kits of parts, the delivery and/or injection system.

17 Claims, 3 Drawing Sheets

DELIVERY SYSTEM FOR PROVIDING SELF-HARDENING CALCIUM SILICATE BASED COMPOSITIONS USED IN MEDICAL APPLICATIONS

FIELD

The present invention relates to the field of delivery and/or injection systems, preferably for medical applications. Especially, the present invention refers to a kit of parts for providing a dental composition able to self-hardening. The kit of parts of the invention comprises a first waterproof container including an anhydrous calcium silicate phase; and a second container comprising an aqueous phase. The kit of parts of the invention may be used in delivery and/or injection systems so that it delivers a homogenous calcium silicate-based composition having a volume ratio between the calcium silicate phase and the aqueous phase ranging from 1 to 3.

The present invention also refers to the hardened material obtained from the kits of parts, the delivery and/or injection system of the invention.

BACKGROUND

Endodontics (also called root canal treatment) is a dental procedure implemented when the pulp (the soft tissue inside a root canal) becomes inflamed or infected. Especially, an endodontic treatment aims to care a tooth while avoiding its extraction from the patient's mouth and includes:
  opening the crown of the tooth;
  removing the damaged pulp until the pulp chamber and the root canals are empty; and
  filling and sealing the root canals and foramen with a suitable dental material.

Among available dental material on the market, the part of calcium silicate-based cements has strongly increased. Indeed, these materials feature good sealing ability and biocompatibility compared to other dental products such as calcium phosphate-based cements and/or resin materials. Besides, compared to cements comprising phosphorus compound such as calcium phosphate cement, calcium silicate-based cements show improved mechanical and rheological properties.

The Applicant has a strong expertise in the manufacturing of dental materials, in particular in endodontics. For example, WO2012/065946 deals with a calcium silicate-based composition useful for filling a root canal, comprising on the one hand, a calcium silicate powder phase; and on the other hand, an aqueous liquid phase.

The composition of WO2012/065946 has improved sealing and handling properties, and is compatible with retreatment procedures. Furthermore, this composition features good adhesion properties so that it is easy to use it either with Gutta Percha points (mono- or multicone), or without Gutta Percha points as a monoblock.

However, the composition of WO2012/065946, such as many other dental materials for endodontics in prior art, is separately packaged. Consequently, the practitioner has to extemporaneously mix the solid phase and the liquid phase before incorporating the dental material inside the patient's mouth. This mixing step is time-consuming and user dependent.

Furthermore, the hardening process resulting from the hydration of calcium silicate particles may be affected by the variability of water content in the final composition after mixing.

Thus, there is always a need for providing alternative dental compositions and/or products easier to use for practitioners. Furthermore, there is always a need for providing dental compositions and/or products featuring a reduced setting time. It is also desirable to provide devices for delivering a calcium silicate-based composition, that may be used by the practitioner for one patient or more.

In the context of the investigations that the Applicant is conducting for constantly optimizing calcium silicate-based compositions, the Applicant has manufactured a kit of parts and an injection system suitable for providing a calcium silicate cement overcoming the drawbacks as mentioned above. Especially, the kit of parts of the invention comprises in a first container, an anhydrous calcium silicate semi-solid comprising tricalcium silicate particles, a non-aqueous or anhydrous carrier and optionally, a radiopacifier; and in a second container, an aqueous semi-solid comprising purified water, a radiopacifier, and a set accelerator.

Advantageously, the kit of parts used in an injection system of the invention is ready for use by the practitioner. Advantageously, the injection system of the invention allows mixing the two pastes of the kit of parts of the invention, and in the same time, delivering the resulting calcium silicate-based composition with the suitable consistency for being directly and easily injected in the body of a subject in need thereof. Advantageously, the kit of parts of the invention provides a dental cement/composition having a suitable consistency for being injected in the body of a subject in need thereof. Advantageously, the kit of parts of the invention provides a hardened dental material having a reduced setting time compared to other dental calcium silicate-based cement resulting from prior art mixtures of powder and liquid phases.

SUMMARY

This invention thus relates to a kit of parts for providing a calcium-silicate based cement, said kit of parts comprising a first container and a second container, wherein:
  the first container is waterproof and comprises an anhydrous calcium silicate semi-solid comprising calcium silicate particles, preferably tricalcium silicate particles, dicalcium silicate particles or any mixtures thereof, a non-aqueous carrier and optionally, a radiopacifier;
  the second container comprises an aqueous semi-solid comprising purified water, a radiopacifier, and a set accelerator;
  the volume ratio between the anhydrous calcium silicate semi-solid and the aqueous semi-solid ranges from 1 to 10, preferably from 1 to 5, more preferably is about 1; and
  provided that said first and second containers do not comprise any phosphorus compounds.

According to one embodiment, the present invention also concerns a delivery system for delivering a self-hardening calcium-silicate based cement, said delivery system comprising the kit of parts of the invention and a mixing chamber.

According to one embodiment, the present invention thus concerns a delivery system for delivering a self-hardening calcium-silicate based cement, a first container, a second container and a mixing chamber, wherein:
  the first container is waterproof and comprises an anhydrous calcium silicate semi-solid comprising calcium silicate particles, preferably tricalcium silicate particles, dicalcium silicate particles or any mixtures thereof, a non-aqueous carrier and optionally, a radiopacifier;

the second container comprises an aqueous semi-solid comprising purified water, a radiopacifier, and a set accelerator;

the volume ratio between the anhydrous calcium silicate semi-solid and the aqueous semi-solid ranges from 1 to 10, preferably from 1 to 5, more preferably is about 1; and provided that said first and second containers do not comprise any phosphorus compounds.

According to one embodiment, the delivery system further comprises a plunger.

According to one embodiment, the first and second containers do not comprise any phosphate.

According to one embodiment, the non-aqueous carrier is selected from glycol compounds and/or silicones and mixtures thereof, preferably the non-aqueous solvent is a glycol compound, more preferably is propylene glycol.

According to one embodiment, the size of calcium silicate particles ranges from 0.01 µm to 50 µm, preferably from 0.1 µm to 30 µm, more preferably from 0.1 µm to 10 µm. According to one embodiment, the size of tricalcium silicate particles ranges from 0.01 µm to 50 µm, preferably from 0.1 µm to 30 µm, more preferably from 0.1 µm to 10 µm. According to one embodiment, the size of particles is measured with a Malvern® granulometer.

According to one embodiment, the radiopacifier is selected from the group comprising bismuth oxide, strontium carbonate, barium sulfate, tantalum oxide, cerium oxide, tin oxide, zirconium oxide compounds and radiopaque glasses containing tantalum, barium and strontium, and mixtures thereof, preferably the radiopacifier is bismuth derivatives, such as for example bismuth oxides or bismuth carbonates or mixtures thereof, or zirconium derivatives, especially zirconium oxide alone or in combination with yttrium; or a mixture of bismuth derivatives and zirconium derivatives.

According to one embodiment, the set accelerator is selected from calcium carbonate, calcium oxide, sodium bicarbonate, calcium lactate, calcium chloride and mixtures thereof, preferably is calcium chloride.

According to one embodiment, the calcium silicate semi-solid and/or the aqueous semi-solid further comprises additives, preferably selected from pH stabilizing agents, set accelerators, surfactants, fillers, texturing/thickening agents, water-reducing agents and mixtures thereof.

According to one embodiment, wherein the first container comprises a calcium silicate semi-solid consisting of:
from 50 to 90% of tricalcium silicate particles;
from 10 to 50% of non-aqueous carrier, preferably selected from glycol, more preferably is propylene glycol;
from 0% to 25% of a radiopacifier; and
from 0% to 5% of additives; by weight to the total weight of the calcium silicate semi-solid; and
wherein the second container comprises an aqueous semi-solid consisting of:
from 10 to 50% of purified water;
from 10 to 75% of a set accelerator, preferably calcium chloride;
from 10% to 80% of a radiopacifier, preferably zirconium oxide; and
from 0% to 20% of additives; by weight to the total weight of the aqueous semi-solid.

According to one embodiment, the first container comprises an anhydrous calcium silicate semi-solid consisting of tricalcium silicate particles and propylene glycol; and the second container comprises an aqueous semi-solid consisting of purified water, calcium chloride, zirconium oxide and additives.

The present invention also concerns a delivery system for delivering a self-hardening calcium-silicate based cement, said system comprising the kit of parts as defined above.

The present invention also refers to the use of the kit of parts and/or the delivery system as defined above, for treating a bone and/or dental disorder or disease in a subject in need thereof; preferably in bone and/or dental restoration or in bone and/or dental filling.

According to one embodiment, the kit of parts of the invention or the delivery system of the invention, is suitable for treating a bone and/or dental disorder or disease in a subject in need thereof.

The present invention also refers to a hardened material obtainable by the kit of parts or the delivery system as defined above.

According to one embodiment, the hardened dental material has a compressive strength ranging from more than 0 to 300 MPa, preferably ranging from 0.5 to 100 MPa, more preferably ranging from 0.5 to 30 MPa.

In the present invention, the following terms have the following meanings:

"About" preceding a figure means plus or less 10% of the value of said figure.

"Additives" refers to any substance added in low amount in a composition for improving its physicochemical properties depending on its use.

"Anhydrous" or "non-aqueous": refers to any water-free or substantially non-hydrated compound or material. Especially, in the present invention, the terms "anhydrous semi-solid" or "non-aqueous semi-solid" mean that there is no hydrated or liquid water in said semi-solid. The term "non-hydrated" further means that said compound or material has not been contacted with any water molecules.

"Bone": refers to rigid organs that constitute part of the endoskeleton of vertebrates. For instance, the term "bone" encompasses bone, mandibular bone, spongious bone and membranous bone.

"Bone or dental restoration": respectively refers to the reconstruction bone or dental tissues by either strengthening the tissue structure or filling a substance loss.

"Bone regeneration": refers to the induction in vivo of the formation of a new self-generating bone tissue.

"Calcium silicate particle": refers to an assembly comprising one or more calcium silicate compounds. The terms "calcium silicate particle" also include assemblies consisting of one or more calcium silicate compounds. According to one embodiment, the calcium silicate particles are selected from tricalcium silicate particles, dicalcium silicate particles and any mixtures thereof.

"Calcium silicate-based cement": refers to any composition that comprises a calcium silicate compound and that hardens when contacting with water. According to the invention, "calcium silicate-based cement" refers to composition for which the hardening only results from the hydration of at least one calcium silicate compound and of the production of calcium silicate hydrate (CSH). According to one embodiment, the calcium silicate-based cement does not comprise any resin material.

"Delivery system": refers to a device comprising or consisting of a mixing system and/or a mixing chamber, at least one cartridge and an aperture. According to one embodiment, the delivery system is a device with an aperture comprising the association of a kit of parts with a mixing system and/or a mixing chamber.

"Impermeable": refers to a material resistant to water penetration and wetting past its momentary contact with water droplets or spray.

"Injection system": refers to a device comprising or consisting of a mixing system and/or a mixing chamber, a cartridge, and a plunger. In the present invention, the terms "injection system" includes double syringe. According to one embodiment, the injection system comprises an aperture. According to one embodiment, the injection system comprises two cartridges, preferably two cartridges and one of which is impermeable or waterproof. According to one embodiment, the injection system comprises the association of a kit of parts with a mixing system and/or a mixing chamber; and a plunger.

"Filler": refers to a solid substance, non-miscible and mechanically dispersed in a matrix.

"Glycol" or "diol": refers to any compound having two hydroxyl groups carried out by different carbon atoms. According to one embodiment, the term "glycol" includes vicinal diol, i.e. compound having two hydroxyl group carried out by two adjacent carbon atoms.

"Hardened dental material": refers to a material suitable for dental applications that is under a solid form. According to one embodiment, the hardened dental material is characterized by a compressive strength ranging from more than 0 to 300 MPa, preferably ranging from 0.5 to 100 MPa, more preferably ranging from 0.5 to 30 MPa.

"Phosphate": refers to a salt or ester of phosphoric acid of formula $H_2PO_4$. Especially, the term "phosphate" refers to a compound comprising a $PO_4^{3-}$ group or related to an anion or a group comprising —$OPO(OH)_2$.

"Phosphorus": refers to nonmetallic chemical element of atomic number 15 and compounds thereof.

"Polymer": refers to any chain or material having a high molecular weight and resulting from the multiple repetition of a repeating unit (monomer), said monomers being covalently linked each other.

"Radiopacifier": refers to a substance added to a material in order to make it opaque, especially to make it visible under X-ray imaging.

"Semi-solid": refers to a substance having a viscosity and rigidity intermediate between that of a solid and of a liquid. In the present invention, the semi-solid compositions refer to compositions having a viscosity so that it is possible to be extruded by a delivery system, preferably by an injection system such as a syringe or a double syringe. In one embodiment, the semi-solid has a viscosity ranging from 10 to $10^5$ Pa·s at about 25° C., preferably ranging from 10 to $10^3$ Pa·s at about 25° C. According to one embodiment, the semi-solid is a paste. According to one embodiment, the semi-solid is not a powder. According to one embodiment, the semi-solid is not a liquid.

"Set accelerator": refers to an agent which reduces the setting time of a material when added to said material.

"Silicone" (also called "polysiloxan"): refers to an inorganic polymer comprising a chain of alternated silicon and oxygen atoms (the repeating unit is -Si—O—).

"Size": refers to the average diameter of a particle.

"Stabilizing agent": refers to a substance able to chemically and/or physically keep a composition stable over time. A "pH stabilizing agent" refers to a substance able to keep the pH of a composition stable overtime.

"Subject": refers to a warm-blooded animal, more preferably a human. Preferably, the subject is a patient, i.e. the subject is awaiting the receipt of, or is receiving medical care or is/will be the object of a medical procedure.

"Surfactant": refers to amphiphilic molecules having two parts of different polarity: one lipophilic and apolar, and the other hydrophilic and polar.

"Treatment" or "Treating": refers to therapeutic treatment wherein the object is to cure or slow down (lessen) the targeted pathologic condition or disorder. A subject or mammal is successfully "treated" for the condition or disorder if, after receiving the dental composition or hardened dental material of the present invention, the patient shows observable and/or measurable reduction in one or more of the symptoms associated with the specific disease or condition; and improvement in quality of life issues. The above parameters for assessing successful treatment and improvement in the disease or conditions are readily measurable by routine procedures familiar to a physician.

"Tricalcium silicate": refers to the chemical compound of formula $Ca_3SiO_9$.

"Texturing agent": refers to a substance allowing giving a structure, and/or consistence to a composition.

"Thickening agent": refers to a substance able to thick a composition.

"Water-reducing agent": refers to a substance able to improve the rheological properties of a composition. Especially, the "water-reducing agent" may be a plastifying or fluidifying agent.

"Waterproof": refers to a material resistant to water penetration and wetting past its continuous contact with water droplets, spray or vapor.

BRIEF DESCRIPTION OF THE DRAWINGS

The foregoing brief description, as well as the following detailed description of the invention, will be better understood when read in conjunction with the appended drawings. For the purpose of illustrating the invention, there are shown in the drawings, certain embodiments which are presently preferred. It should be understood, however, that the invention is not limited to the precise arrangements and instrumentalities shown.

FIG. 1 is a photograph showing the right side of the injection system of the invention. The injection system comprises a mixing system (2), a cartridge (3) and a plunger (4). The mixing system (2) includes a mixing nozzle (21) and a discharging outlet (22). The mixing nozzle (21) mixes the materials of the first container (31) and the second container (32), said first and second containers being encompassed in the cartridge (3). The cartridge (3) comprises in one end an aperture so that the plunger (4) including the pushers (41), may be inserted into the cartridge (3). On the other end, the cartridge (3) is connected to the mixing tip for extruding the dental composition resulting from the mixture of each semi-solid contained in the first and the second containers.

FIG. 4 is a photograph showing the kit of parts of the invention. The kit of parts (5) comprises at least two containers (51 and 52). Each container presents a male thread system (53) to be hermetically sealed by means of a cap (54) presenting a female thread system of a cap.

DETAILED DESCRIPTION

Compositions

This invention relates to a composition used for medical and/or pharmaceutical applications. According to one embodiment, the composition of the invention is a calcium silicate-based composition, preferably a self-hardening calcium silicate-based cement. According to one embodiment, the composition of the invention is a dental composition.

Especially, the present invention refers to a composition, preferably a dental composition, resulting from the mixture of an anhydrous calcium silicate phase and an aqueous phase.

According to one embodiment, the composition results from the mixture comprising or consisting of:
  an anhydrous calcium silicate phase comprising calcium silicate particles, at least one non-aqueous carrier and optionally, a radiopacifier; and
  an aqueous phase comprising purified water, at least one radiopacifier, and at least one set accelerator.

According to one embodiment, the composition results from the mixture comprising or consisting of:
  an anhydrous calcium silicate phase comprising calcium silicate particles, at least one non-aqueous carrier, at least one thickening agent and, optionally at least one of a radiopacifier, a jellifying agent, a surfactant and/or a setting accelerator; and
  an aqueous phase comprising purified water, at least one radiopacifier, at least one set accelerator and at least one jellifying agent.

According to one embodiment, the volume ratio between the calcium silicate phase and the aqueous phase ranges from 1 to 10, preferably from 1 to 5, more preferably is about 1. According to one embodiment, the volume ratio between the calcium silicate phase and the aqueous phase is 1.0; 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9 or 3. According to one embodiment, the volume ratio between the calcium silicate phase and the aqueous phase is 1, 2, 3, 4, 5, 6, 7, 8, 9 or 10.

According to one embodiment, the composition does not comprise any phosphate or phosphorus compounds.

According to one embodiment, the composition further comprises additives. According to one embodiment, the composition further comprises a mixture of at least one set accelerator and cellulose or derivatives thereof.

Calcium Silicate Phase

According to one embodiment, the anhydrous calcium silicate phase comprises or consists of calcium silicate particles, a non-aqueous carrier and optionally, a radiopacifier. According to one embodiment, the anhydrous calcium silicate phase comprises or consists of calcium silicate particles, a non-aqueous carrier, a thickening agent and optionally, a radiopacifier, a jellifying agent and/or a setting accelerator.

According to one embodiment, the anhydrous calcium silicate phase is a semi-solid or solid phase. According to a specific embodiment, the anhydrous calcium silicate phase is a semi-solid phase, preferably is a paste. According to an embodiment, the anhydrous calcium silicate phase is not under the form of a powder.

According to one embodiment, the calcium silicate particles in the calcium silicate phase comprise or consist of tricalcium silicate particles (C3S). According to one embodiment, the calcium silicate particles in the calcium silicate phase comprise or consist of tricalcium silicate particles (C3S), dicalcium silicate (C2S) and any mixtures thereof.

According to one embodiment, the size of the calcium silicate particles ranges from 0.01 μm to 50 μm, preferably from 0.1 μm to 30 μm, more preferably from 0.1 μm to 10 μm. According to one embodiment, the size of the calcium silicate particles is about 0.1; 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 μm. According to one embodiment, the size of the calcium silicate particles is about 0.1; 1, 2, 3, 4, 5, 6, 7, 8, 9 or 10 μm. According to one embodiment, the size of the calcium silicate particles is about 0.1; 5, 10, 15, 20, 25 or 30 μm. According to one embodiment, the size of the calcium silicate particles is about 0.1; 0.2; 0.3; 0.4; 0.5; 0.6; 0.7; 0.8; 0.9 or 1 μm.

According to one embodiment, the size of tricalcium silicate particles ranges from 0.01 μm to 50 μm, preferably from 0.1 μm to 30 μm, more preferably from 0.1 μm to 10 μm. According to one embodiment, the size of tricalcium silicate particles is about 0.1; 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 μm. According to one embodiment, the size of tricalcium silicate particles is about 0.1; 1, 2, 3, 4, 5, 6, 7, 8, 9 or 10 μm. According to one embodiment, the size of tricalcium silicate particles is about 0.1; 5, 10, 15, 20, 25 or 30 μm. According to one embodiment, the size of tricalcium silicate particles is about 0.1; 0.2; 0.3; 0.4; 0.5; 0.6; 0.7; 0.8; 0.9 or 1 μm.

According to one embodiment, the calcium silicate phase comprises from 30 to 90%, preferably from 40 to 90%, from 50 to 90%, from 60 to 90%, from 70 to 90%, from 80 to 90%, from 55 to 85%, from 60 to 80% of calcium silicate particles, such as C3S, C2S or any mixtures thereof, in weight to the total weight of said calcium silicate phase. According to one embodiment, the calcium silicate phase comprises from 30 to 80%, preferably from 30 to 70%, from 30 to 60%, from 30 to 50%, from 30 to 40% of calcium silicate particles, such as C3S, C2S or any mixtures thereof, in weight to the total weight of said calcium silicate phase. According to one embodiment, the calcium silicate phase comprises 50; 55; 60; 65, 70, 75; 80; 85 or 90% of calcium silicate particles, such as C3S, C2S or any mixtures thereof, in weight to the total weight of said calcium silicate phase. According to one embodiment, the calcium silicate phase comprises 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90% of calcium silicate particles such as C3S, C2S or any mixtures thereof, in weight to the total weight of said calcium silicate phase.

According to one embodiment, the calcium silicate phase comprises from 30 to 90%, preferably from 40 to 90%, from 50 to 90%, from 60 to 90%, from 70 to 90%, from 80 to 90%, from 55 to 85%, from 60 to 80% of tricalcium silicate particles in weight to the total weight of said calcium silicate phase. According to one embodiment, the calcium silicate phase comprises from 30 to 80%, preferably from 30 to 70%, from 30 to 60%, from 30 to 50%, from 30 to 40% of tricalcium silicate particles in weight to the total weight of said calcium silicate phase. According to one embodiment, the calcium silicate phase comprises 50; 55; 60; 65, 70, 75; 80; 85 or 90% of tricalcium silicate particles in weight to the total weight of said calcium silicate phase. According to one embodiment, the calcium silicate phase comprises 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90% of tricalcium silicate particles in weight to the total weight of said calcium silicate phase.

According to one embodiment, the non-aqueous carrier is a non-aqueous liquid. According to one embodiment, the non-aqueous carrier does not comprise any resin material.

The mixture of the solid calcium silicate particles with the liquid non-aqueous carrier results in the anhydrous calcium silicate phase under the form of a semi-solid, as defined above, preferably a paste.

The mixture of the solid tricalcium silicate particles with the liquid non-aqueous carrier results in the anhydrous calcium silicate phase under the form of a semi-solid, as defined above, preferably a paste.

According to one embodiment, the non-aqueous carrier comprises or consists of glycerol, glycol compounds and/or silicones or mixture thereof, preferably the non-aqueous carrier is a glycol compound, more preferably is propylene glycol.

According to one embodiment, the glycol compound is selected from ethylene glycol, propylene glycol (or propane-1,2-diol), trimethylene glycol (or propane-1,3-diol), butylene glycol (orbutane-1,3-diol), butane-1,2-diol, butane-1,4-diol, pentylene glycol (or pentane-1,5-diol), pentane-1,2-diol, pentane-1,3-diol, pentane-1,4-diol dipropylene glycol; preferably the glycol compound ispropylene glycol or dipropylene glycol.

According to one embodiment, the silicone is selected from alkylsilicone, more preferably selected from methicone, dimethylmethicone, caprylylmethicone or their copolymers or mixtures thereof. According to one embodiment, the silicone is selected from methicone, dimethylmethicone and caprylylmethicone.

According to one embodiment, the calcium silicate phase comprises from 10 to 50%, preferably from 20 to 50%, preferably from 30 to 50%, preferably from 40 to 50%, preferably 10, 15, 20, 25, 30, 35, 40, 45 or 50%, of a non-aqueous carrier in weight to the total weight of said calcium silicate phase. According to one embodiment, the calcium silicate phase comprises 20; 21; 22; 23; 24; 25; 26; 27; 28; 29; 30; 31; 32; 33, 34, 35; 36; 37; 38; 39; 40; 41; 42; 43; 44; 45; 46; 47; 48; 49 or 50% of a non-aqueous carrier in weight to the total weight of said calcium silicate phase.

According to one embodiment, the radiopacifier is selected from the group comprising bismuth oxide, strontium carbonate, barium sulfate, tantalum oxide, cerium oxide, tin oxide, zirconium oxide compounds and radiopaque glasses containing tantalum, barium and strontium, and mixtures thereof, preferably the radiopacifier is bismuth derivatives, such as for example bismuth oxides or bismuth carbonates or mixture thereof, or zirconium derivatives, especially zirconium oxide alone or in combination with yttrium; or a mixture of bismuth derivatives and zirconium derivatives.

According to one embodiment, the amount of radiopacifier in the calcium silicate phase ranges from 0% to 25%, preferably from 1% to 15%, from 5% to 10% by weight to the total weight of the calcium silicate phase. According to one embodiment, the amount of radiopacifier in the calcium silicate phase ranges from 0% to 20%, preferably from 1% to 20%, from 5% to 20%, from 10% to 20%, from 15% to 20% by weight to the total weight of the calcium silicate phase. According to one embodiment, the amount of radiopacifier in the calcium silicate phase is of about 1, 2, 3, 4, 5, 6, 7, 8, 9, 10, 11, 12, 13, 14, 15, 16, 17, 18, 19 or 20% by weight to the total weight of the calcium silicate phase.

According to one embodiment, the calcium silicate phase comprises from 0 to 25%, preferably from 5 to 20%, preferably from 10 to 20%, preferably from 15 to 20%, preferably 1, 2, 3, 4, 5, 6, 7, 8, 9, 10, 11, 12, 13, 14, 15, 16, 17, 18, 19 or 20%, of radiopacifier in weight to the total weight of said calcium silicate phase.

According to one embodiment, the calcium silicate phase further comprises additives, such as for example those listed hereafter. According to one embodiment, the calcium silicate phase comprises from 0 to 5%, preferably 1, 2, 3, 4 or 5%, of at least one additive in weight to the total weight of said calcium silicate phase. According to one embodiment, the calcium silicate phase comprises 0.1; 0.2; 0.3; 0.4; 0.5; 0.6; 0.7; 0.8; 0.9, 1; 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9; 3; 3.1; 3.2; 3.3; 3.4; 3.5; 3.6; 3.7; 3.8; 3.9; 4; 4.1; 4.2; 4.3; 4.4; 4.5; 4.6; 4.7; 4.8; 4.9 or 5%, of at least one additive in weight to the total weight of said calcium silicate phase.

According to one embodiment, the calcium silicate phase consists of:
  from 50 to 90% of a mixture of dicalcium silicate particles and tricalcium silicate particles;
  from 10 to 50% of non-aqueous carrier;
  from 0% to 25% of a radiopacifier; and
  from 0% to 5% of additives; by weight to the total weight of the calcium silicate phase.

According to one embodiment, the calcium silicate phase consists of:
  from 50 to 90% of dicalcium silicate particles;
  from 10 to 50% of non-aqueous carrier;
  from 0% to 25% of a radiopacifier; and
  from 0% to 5% of additives; by weight to the total weight of the calcium silicate phase.

According to one embodiment, the calcium silicate phase consists of:
  from 50 to 90% of tricalcium silicate particles;
  from 10 to 50% of non-aqueous carrier;
  from 0% to 25% of a radiopacifier; and
  from 0% to 5% of additives; by weight to the total weight of the calcium silicate phase.

Aqueous Phase

According to one embodiment, the aqueous phase comprises purified water, a radiopacifier, and a set accelerator.

According to one embodiment, the aqueous phase is a semi-solid or a solid phase. According to a preferred embodiment, the aqueous phase is a semi-solid, preferably is a paste. According to an embodiment, the aqueous phase is not under the form of a liquid.

According to another embodiment, the aqueous phase is a liquid phase.

According to one embodiment, the set accelerator comprises or consists of calcium carbonate, calcium oxide, sodium bicarbonate, calcium lactate and calcium chloride or mixtures thereof, preferably is calcium chloride.

According to one embodiment, the radiopacifier present in the aqueous phase is as listed above with regards to the calcium silicate phase.

According to one embodiment, the aqueous semi-solid comprises from 10 to 50%, preferably from 20 to 50%, preferably from 30 to 50%, preferably from 40 to 50%, of purified water in weight to the total weight of said aqueous semi-solid. According to one embodiment, the aqueous semi-solid comprises 10; 15; 20; 25, 30, 35; 40; 45 or 50% of purified water in weight to the total weight of said aqueous semi-solid. According to one embodiment, the aqueous semi-solid comprises 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% of purified water in weight to the total weight of said aqueous semi-solid.

According to one embodiment, the aqueous semi-solid comprises from 10 to 50%, preferably from 20 to 50%, preferably from 30 to 50%, preferably from 40 to 50%, of a set accelerator in weight to the total weight of said aqueous semi-solid. According to one embodiment, the aqueous semi-solid comprises 10; 15; 20; 25, 30, 35; 40; 45 or 50% of a set accelerator in weight to the total weight of said aqueous semi-solid. According to one embodiment, the aqueous semi-solid comprises 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50% of a set accelerator in weight to the total weight of said aqueous semi-solid.

According to one embodiment, the aqueous semi-solid further comprises additives, such as for example those listed hereafter. According to one embodiment, the aqueous semi-solid comprises from 0 to 20%, preferably from 5 to 20%, preferably from 10 to 20%, preferably from 15 to 20%, preferably 1, 2, 3, 4, 5, 6, 7, 8, 9, 10, 11, 12, 13, 14, 15, 16, 17, 18, 19 or 20%, of at least one additive in weight to the total weight of said aqueous semi-solid.

According to one embodiment, the aqueous semi-solid consists of:
from 10 to 50% of purified water;
from 10 to 50% of a set accelerator;
from 10% to 75% of a radiopacifier; and
from 0% to 20% of additives; by weight to the total weight of the aqueous semi-solid.

Additives

According to one embodiment, the calcium silicate phase and/or the aqueous phase further comprises additives, preferably selected from pH stabilizing agents, set accelerators, surfactants, fillers, texturing agents, thickening agents, jellifying agents and water-reducing agents.

According to one embodiment, the pH stabilizing agent is a mineral acid or an organic acid.

According to one embodiment, the set accelerator is selected from calcium carbonate, calcium oxide, sodium bicarbonate, calcium lactate, calcium chloride and mixtures thereof, preferably is calcium chloride.

According to one embodiment, the surfactant is a polysorbate.

According to one embodiment, the texturing agent is selected from silica, povidone, celluloses, or polymers such as acrylamide/sodium acryloyldimethyltaurate copolymer isohexadecane, hydroxyethyl acrylate/sodium acryloyl dimethyl taurate copolymer.

According to one embodiment, the thickening agent is selected from mineral fillers, fumed silica (hydrophilic and/or hydrophobic), and thickening polymers such as polyvinylpyrrolidone (PVP). According to one embodiment, the thickening agent in the calcium silicate phase is selected from fumed silica (hydrophilic and/or hydrophobic), and thickening polymers such as polyvinylpyrrolidone (PVP). According to one embodiment, the calcium silicate phase comprises 0.5% of a thickening agent, preferably 0.5% of hydrophilic fumed silica, by weight to the total weight of the calcium silicate phase. According to one embodiment, the calcium silicate phase comprises from 1 to 3% % of at least one thickening agent, preferably from 1 to 3% % of a mixture of hydrophilic fumed silica, hydrophobic fumed silica and/or PVP, by weight to the total weight of the calcium silicate phase.

According to one embodiment, the jellifying agent is selected from cellulose or derivatives thereof, such as for example methylcellulose, hydroxypropylcellulose and hydroxyethylcellulose; or xanthan gum, or their mixtures.

According to one embodiment, the water-reducing agent is selected from calcium silicate hydrates, hydrophilic copolymers, vinyl polymer.

Mixture

According to one embodiment, the composition of the invention comprises an anhydrous calcium silicate semi-solid consisting of calcium silicate particles, preferably dicalcium silicate particles, tricalcium silicate particles or any mixtures thereof; and propylene glycol; and an aqueous semi-solid consisting of purified water, calcium chloride, zirconium oxide and optionally additives.

According to one embodiment, the composition of the invention comprises an anhydrous calcium silicate semi-solid consisting of tricalcium silicate particles and propylene glycol; and an aqueous semi-solid consisting of purified water, calcium chloride, zirconium oxide and optionally additives.

According to one embodiment, the calcium silicate semi-solid, the aqueous semi-solid and/or the dental composition is (are) consistent. According to one embodiment, the calcium silicate semi-solid, the aqueous semi-solid and/or the composition of the invention is (are) creamy. According to one embodiment, the calcium silicate semi-solid, the aqueous semi-solid and/or the composition of the invention is (are) colored, preferably white.

According to one embodiment, the calcium silicate semi-solid, the aqueous semi-solid and/or the dental composition has (have) a viscosity at about 25° C. ranging from 10 to $10^5$ Pa·s, preferably ranging from 10 to $10^3$ Pa·s. In the present invention, the viscosity is measured by the Anton Paar MCR 102 rheometer. According to one embodiment, the calcium silicate semi-solid, the aqueous semi-solid and/or the composition of the invention has (have) a viscosity is about 10, $10^2$, $10^3$, $10^4$ or $10^5$ Pa·s.

In the present invention, the mixture of the anhydrous calcium silicate phase and the aqueous phase of the invention provokes the hardening of the composition and provides a hardened material, preferably a hardened dental material.

According to one embodiment, the setting time of the composition of the invention ranges from 30 min to 72 h, preferably from 45 min to 4 h.

Kit of Parts

In a second aspect, this invention relates to a kit of parts for manufacturing the previously described compositions of the invention. According to one embodiment, the kit of parts of the invention comprises at least two containers: the first container comprising an anhydrous calcium silicate phase as defined above; and the second container comprising an aqueous phase as defined above.

According to one embodiment, the kit of parts comprises at least one container filled with an anhydrous calcium silicate phase, preferably an anhydrous calcium silicate semi-solid, comprising calcium silicate particles, a non-aqueous carrier and optionally a radiopacifier, as previously described. According to one embodiment, the kit of parts comprises at least one container filled with an anhydrous calcium silicate phase, preferably an anhydrous calcium silicate semi-solid, comprising tricalcium silicate particles, a non-aqueous carrier and optionally a radiopacifier, as previously described. According to one embodiment, the kit of parts comprises at least one container filled with an aqueous semi-solid comprising purified water, a radiopacifier, and a set accelerator, as previously described.

According to one embodiment, the container is made of any compressible material known in the art allowing them to release the contained phase when external pressure is applied onto them. According to one embodiment, the anhydrous calcium silicate phase and/or the aqueous phase contained in the containers is (are) extruded upon external pressure on the surface of the container. According to one embodiment, the kit of parts further comprises adequate sealing caps for its containers. According to one embodiment, at least one of the containers of the kit of parts is waterproof.

Figure 4:
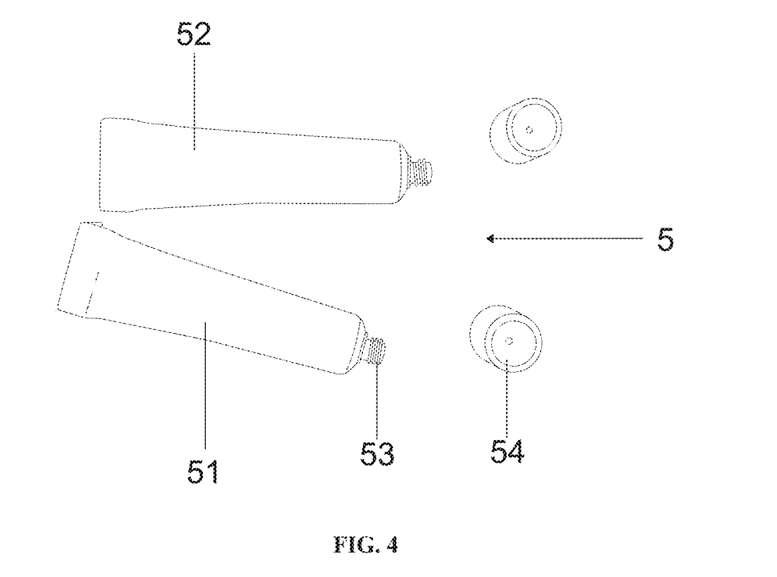

According to one embodiment, the container(s) is (are) tube-shape formed, for example as depicted in FIG. 4. According to one embodiment, the aperture of the container can be hermetically isolated from the external environment by means of a thread system. According to one embodiment, the thread system comprises a male thread exit of the container and a female thread system on the cap.

According to one embodiment, the size of the container(s) can be adjusted to the needed volume of composition to be used. According to one embodiment, the size of the at least one container of the kit of parts is adequate for filling a cartridge of a delivery and/or injection system. According to one embodiment, the containers of the kit have the suitable dimensions to be included in a delivery and/or injection system.

According to one embodiment, the kit of parts for manufacturing the previously described compositions of the invention, is reusable.

Delivery System/Injection System

In a third aspect, this invention relates to a delivery system, preferably an injection system such as for example a syringe or a double-syringe.

According to one embodiment, the delivery system and/or the injection system is able to provide the composition of the invention as defined above, preferably by mixture and extrusion of an anhydrous calcium silicate phase and an aqueous phase.

Advantageously, the delivery system and/or the injection system of the invention does not imply that the practitioner has to premix the calcium silicate paste with the aqueous liquid paste before its use. Consequently, the delivery system and/or the injection system of the invention provides a more efficient tool for the practitioner.

According to one embodiment, the delivery system and/or the injection system is able to provide the composition of the invention as defined above, for one or more patients. Advantageously, the delivery system and/or the injection system of the invention may be reused by the practitioner by changing the nozzle of said delivery system for each patient. According to one embodiment, the practitioner using the injection system comprising the kit of parts of the invention, may use the accurate amount of the dental product so that the remaining amount of the dental product is not spoiled and may be reused for another patient.

According to one embodiment, the delivery system and/or the injection system is not a unidose delivery system. According to one embodiment, the delivery system and/or the injection system is not a unidose syringe.

In the present invention, the expression "unidose" delivery system" and/or "unidose injection system" refers to a delivery system or an injection system that contains the amount of product or of composition, needed to be used only once. According to the invention, the expression "unidose delivery system" refers to a delivery system that is not able to deliver the composition as defined above, more than once.

According to one embodiment, the delivery system of the invention is for delivering a self-hardening calcium-silicate based cement. According to one embodiment, the delivery system of the invention comprises a first container, a second container and a mixing chamber, wherein:

the first container is waterproof and comprises an anhydrous calcium silicate semi-solid comprising calcium silicate particles, preferably tricalcium silicate particles, dicalcium silicate particles or any mixtures thereof, a non-aqueous carrier and optionally, a radiopacifier;

the second container comprises an aqueous semi-solid comprising purified water, a radiopacifier, and a set accelerator;

the volume ratio between the anhydrous calcium silicate semi-solid and the aqueous semi-solid ranges from 1 to 10, preferably from 1 to 5, more preferably is about 1.

According to one embodiment, the present invention refers to an injection system comprising a mixing system, a cartridge and a plunger comprising two independent pushers; said mixing system comprising a mixing nozzle and a discharging outlet, wherein:

said cartridge comprises a first container and a second container, wherein:

the first container is waterproof and comprises an anhydrous calcium silicate semi-solid comprising calcium silicate particles, preferably tricalcium silicate particles, dicalcium silicate particles or any mixtures thereof, a non-aqueous carrier and optionally, a radiopacifier;

the second container comprises an aqueous semi-solid comprising purified water, a radiopacifier, and a set accelerator;

the volume ratio between the anhydrous calcium silicate semi-solid and the aqueous semi-solid ranges from 1 to 10, preferably is about 1; and According to one embodiment, the anhydrous calcium silicate semi-solid phase and/or the aqueous semi-solid phase does (do) not comprise any resin material. Advantageously, the absence of resin avoids the sensibility issue for some patients regarding these resin materials.

According to one embodiment, when used, the two pushers independently move the anhydrous calcium silicate semi-solid of the first container and the aqueous semi-solid of the second container into the mixing system where they are contacted together in the mixing nozzle resulting in a homogenous dental composition having a volume ratio between the calcium silicate semi-solid and the aqueous semi-solid ranging from 1 to 10, preferably the volume ratio is about 1; said dental composition being delivered through the discharging outlet.

According to one embodiment, the injection system comprising the kit of parts of the invention, such as a double syringe filled with the composition as defined above, is easy to be used. Especially, the injection system of the invention does not require a high extractive strength for extruding the dental material filled inside the injection system. According to one embodiment, the extractive strength required for using the injection system of the invention ranges from more than 0 to 60 N, preferably from 1 N to 50 N, more preferably from 10N to 30N, even more preferably is 22 N. According to one embodiment, the extractive strength required for using the injection system of the invention is about 5, 10, 15, 20, 25, 30, 35, 40, 45, 50 or 55 N. Advantageously, the extractive strength required for using the injection system of the invention is low (lower than 60N) so that it is easy for the practitioner to extrude the dental composition from the injection system.

According to one embodiment, the dental composition does not sediment. According to one embodiment, the dental composition, hardened or not, has an alkaline pH, preferably has a pH ranging from 7 to 14, more preferably ranging from 7 to 12. According to one embodiment, the pH of the tissues surrounding the implanted dental material, measured after 24 h, is alkaline, preferably ranges from 7 to 14, more preferably ranges from 7 to 12. According to one embodiment, the dental material of the invention, hardened or not, limits the bactericidal proliferation. According to one embodiment, the dental composition after being hydrated provides a hardened dental material having good sealing properties, preferably good apical sealing properties. According to one embodiment, the hardened dental material of the invention has an apical sealing after 8 days, ranging from 0 mm to 2 mm, preferably from 1 mm to 1.8 mm, more preferably is 1.5 mm.

Figure 1:
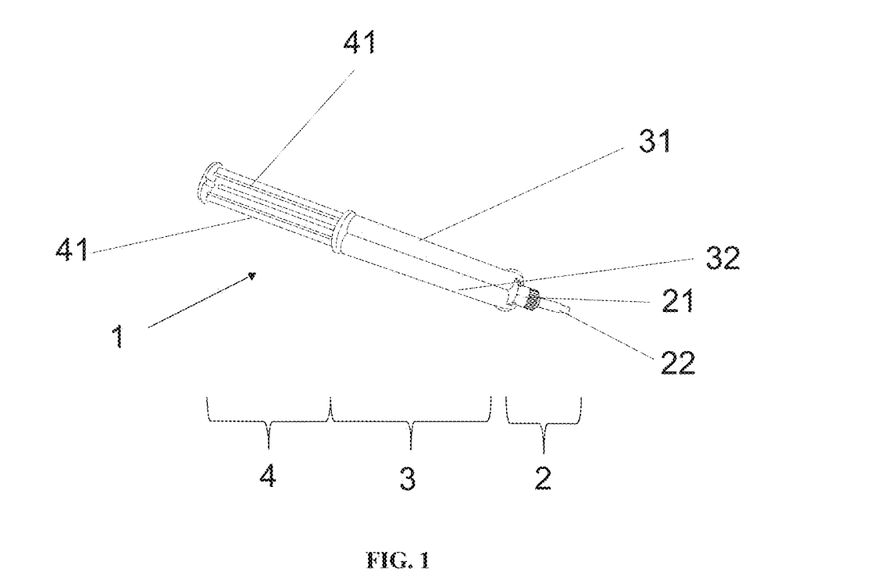

According to one embodiment, the injection system is as depicted in FIG. 1.

According to one embodiment, the first and second containers do not comprise any phosphorus and/or phosphate compounds.

According to one embodiment, the delivery system comprises a plunger. According to one embodiment, the delivery system is an injection system.

According to one embodiment, the delivery system and/or injection system comprises or consists of at least two separated containers, and optionally a mixing nozzle. According to one embodiment, the delivery system and/or the injection system further comprises other containers, preferably a third container. According to one embodiment, the first and/or second container is (are) impermeable. According to one embodiment, the first and/or second container is (are) waterproof.

According to one embodiment, the volume ratio between the calcium silicate semi-solid and the aqueous semi-solid ranges from 1 to 10, preferably from 1 to 5, more preferably is about 1. According to one embodiment, the volume ratio between the calcium silicate semi-solid and the aqueous semi-solid is 1; 1.1; 1.2; 1.3; 1.4; 1.5; 1.6; 1.7; 1.8; 1.9; 2; 2.1; 2.2; 2.3; 2.4; 2.5; 2.6; 2.7; 2.8; 2.9 or 3.

According to one embodiment, the first container is waterproof. According to one embodiment, the first container comprises an anhydrous calcium silicate semi-solid consisting of tricalcium silicate particles and propylene glycol; and the second container comprises an aqueous semi-solid consisting of purified water, calcium chloride, zirconium oxide and additives.

According to one embodiment, the delivery system and/or the injection system further comprises a discharging system. According to one embodiment, the discharging system comprises a mixing chamber and a discharging outlet. According to one embodiment, the discharging system comprises a mixing nozzle or a mixing tip.

According to one embodiment, the mixing nozzle of the delivery system and/or the injection system, is disposable. According to one embodiment, the mixing nozzle of the delivery system and/or the injection system, is reusable.

According to one embodiment, the mixing tip of the delivery system and/or the injection system, is disposable. According to one embodiment, the mixing tip of the delivery system and/or the injection system, is reusable.

Use

The invention also relates to the use of the kit of parts, the delivery system and/or the injection system as defined above, in the medical field such as for example dental field or bone restorative field.

According to one embodiment, the kit of parts, the delivery system and/or the injection system of the invention is for use in the dental field such as endodontic field.

According to one embodiment, the kit of parts, the delivery system and/or the injection system of the invention is for use in treating a bone and/or dental disorder or disease in a subject in need thereof. According to one embodiment, the present invention refers to the use of the kit of parts, the delivery system and/or the injection system of the invention for treating a bone and/or dental disorder or disease in a subject in need thereof. According to one embodiment, the present invention refers to a method for treating a bone and/or dental disorder or disease in a subject in need thereof by using the kit of parts, the delivery system and/or the injection system of the invention as defined above.

According to one embodiment, the kit of parts, the delivery system and/or the injection system of the invention is for use in filling a tooth such as the root canal of a tooth, treating caries or for dental restoration. According to one embodiment, the present invention refers to the use of the kit of parts, the delivery system and/or the injection system of the invention for filling a tooth such as the root canal of a tooth, treating caries or for dental restoration. According to one embodiment, the present invention refers to a method for filling a tooth such as the root canal of a tooth, treating caries or for dental restoration by using the kit of parts, the delivery system and/or the injection system of the invention as defined above.

According to one embodiment, the kit of parts, the delivery system and/or the injection system of the invention is for use in bone restoration or bone regeneration. According to one embodiment, the present invention refers to the use of the kit of parts, the delivery system and/or the injection system of the invention for bone restoration or bone regeneration. According to one embodiment, the present invention refers to a method for bone restoration or bone regeneration by using the kit of parts, the delivery system and/or the injection system of the invention as defined above.

According to one embodiment, the kit of parts, the delivery system and/or the injection system of the invention when used provides a hardened material such as a hardened dental material or a hardened bone regenerative material.

Advantageously, the kit of parts, the delivery system and/or the injection system of the invention when used, provides a material that hardens only after contacting the anhydrous calcium silicate semi-solid with the aqueous semi-solid as defined above. Advantageously, the practitioner using the kit of parts, the delivery system and/or the injection system of the invention does not need to add any water for providing a hardened dental material. Advantageously, the hardening of the composition extruded from the kit of parts, the delivery system and/or the injection system of the invention, is independent from the water amount of surrounding tissues in a subject.

Method for Providing a Dental Material

This invention also relates to a method for providing a material, preferably a dental material or a bone regenerative material, comprising using the kit of parts, the delivery system and/or the injection system of the invention as defined above.

According to one embodiment, the method of the invention provides a self-hardened calcium silicate-based composition. According to one embodiment, the method of the invention provides dental and/or bone implants.

Advantageously, the method of the invention allows providing by easy way dental material used for bone and/or dental restoration or filling.

Hardened Calcium Silicate-Based Material

This invention also relates to a hardened material, preferably a dental and/or bone regenerative and/or restorative material, obtainable by the kit of parts, the delivery system and/or the injection system of the invention as defined above.

According to one embodiment, the hardened material results from the mixture of an anhydrous calcium silicate semi-solid and an aqueous semi-solid, as defined above. According to one embodiment, the calcium silicate phase and the aqueous phase mix together provides the hardening of the material of the invention. According to one embodiment, the hardening of the material of the invention only results from the hydration of the calcium silicate phase as defined above, by the aqueous phase as defined above. According to one embodiment, the hardening of the material of the invention only results from the hydration of the calcium silicate particles, preferably tricalcium silicate particles (C3S), of the calcium silicate phase as defined above, by the aqueous phase as defined above.

According to one embodiment, the hardened material has a compressive strength ranging from ranging from more than 0 to 300 MPa, preferably ranging from 1 to 250 MPa, from 1 to 200 MPa, from 1 to 150 MPa, from 1 to 100 MPa, from 1 to 50 MPa, more preferably ranging from 1 to 30 MPa. According to one embodiment, the hardened material has a compressive strength of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or 300 MPa.

According to one embodiment, the hardened material has a radiopacity ranging from 2 to 15 mm, preferably from 3 to 10 mm, preferably from 4 to 9.5 mm Aluminum. In the present invention, the radiopacity of the hardened material fulfils the standardization of dental materials, especially the specification NF EN ISO 6876.

According to one embodiment, the hardened dental material is able to adhere to one or more Gutta Percha points.

EXAMPLES

The present invention is further illustrated by the following examples.

Abbreviations
C3S: tricalcium silicate;
g: gram(s);
h: hour(s);
ml: milliliter;

Materials and Methods

Extraction Test

The compositions of the invention were extracted from the injection system of the invention. The extraction is evaluated qualitatively: easy, average, difficult or impossible. This parameter evaluates the ease of use of the composition of the invention.

Appearance of Mixture

Mixture quality was evaluated according to the following scale:

| Liquid | Fluid semi-solid | Creamy semi-solid | Consistent semi-solid | Very consistent semi-solid |
|---|---|---|---|---|
| 1 | 2 | 3 | 4 | 5 |

Other parameters were observed such as elasticity, color, adhesion to the instruments, and efficient delivery.

Setting Time

The metal mold of 2 mm thickness with a perforation with a diameter equal to 10 mm, is placed on a glass slide. The sample is extracted from the injection system and inserted into the mold. The whole is placed in a water bath at 37° C. with a humid atmosphere of a minimum of 95% relative humidity. Then, the setting time is measured at regular intervals with a 100 g Gillmore needle.

The setting time is here defined as the period between the introduction of the cement into the water bath and the moment when the penetrator no longer leaves perceptible circular traces on the surface of the sample.

Rheology

To study the rheological behavior of each of the two semi-solids (or pastes) as well as the composition of the invention, and in particular the viscosity, the Anton Paar MCR 102 rheometer is used. The plane-plane mobile PP50 is used. The objective of the method is to obtain a viscosity profile as a function of the defined shear rate of 0.01 to 100 $s^{-1}$.

Radiopacity

The test is carried out according to the NF EN ISO 6876:2012 standard. Sample preparation is carried out in 2 mm thick metal molds with a perforation with a diameter of 10 mm.

pH

The pH is measured using an SCI PRO 007 electrode, suitable for pastes. This measurement is carried out on the anhydrous C3S paste, on the aqueous paste as well as on the mixture of the two. The pH measurement is also carried out on the environment of the dental material, hardened or not, resulting from the kit of parts of the invention.

Compressive Strength

The samples are made in compression molds. The compression test is carried out after molding the sample. The general procedure comprises the following steps:

making the surfaces of the sample flat using the Struers roughing/polishing bench, measuring the length of the sample;

placing the flat ends of the sample between the trays of the mechanical test device (MTS bench); and Performing this test on a series of 4 to 6 samples.

Particle Size Measurement

The size of the C3S particles are measured using a Malvern® granulometer. The size particle distribution is performed using a wet dispersion of the powder in ethanol.

Morphological Characterization of the C3S Particles

First, C3S particles are observed using a MEB.

Then, a morphological characterization is performed using a Morphologi G3 SE Malvern® equipped with an optical bench equipped with:
- 5 Nikon lens;
- One dispersive module.

Specific Area Analysis

Specific area analysis has been performed using the BET nitrogen adsorption method with the GEMINI VII Micromeritics® device.

The method was performed as following:
- Degazing the phase: 1 h at 90° C. then 3 h at 250° C.;
- Temperature during the analysis: −196° C. (Dewar of nitrogen);
- Pression range 0<P/PO<0.25 (PO: saturation vapor pressure of the nitrogen at −196° C.);
- Signal treatment: 5 points, BET method.

Part 1: Chemical Examples

Example 1: Kit of Parts

The compositions of the invention have been made by mixing the content of a first container comprising an anhydrous C3S phase selected from Table 1 with the content of a second container comprising an aqueous phase selected from Table 2. The ratio between the C3S phase and the aqueous phase ranges from more than 1 to 10, preferably from 1 to 5, more preferably the ratio is about 1.

TABLE 1

| | Components | Weight percentage (%) | | | | | | | | | |
|---|---|---|---|---|---|---|---|---|---|---|---|
| | C3S PHASE N° | 1 | 2 | 3 | 4 | 5 | 6 | 7 | 13 | 14 | 16 |
| Calcium silicate | C3S | 50 | 50 | 70 | 50 | 60 | 60 | 60 | 40 | 50 | 60 |
| Radiopacifier | Zirconium oxide | 20 | 15.68 | | 21 | 5.85 | | | 25.85 | 15.85 | 5.85 |
| | Bismuth oxide | | | | | | | | | | |
| | Barium sulfate | | | | | | | | | | |
| Non-aqueous | Caprylylmethicone | | | | | | | | | | |
| carrier | Dimethicone | | | | | | | | | | |
| | Dipropylene glycol | | | | | | | | | | |
| | Glycerol | | | | | | | | | | 32 |
| | Propylene glycol | 27.93 | 33 | 27.93 | 27.93 | 32 | 37 | 37.73 | 32 | 32 | |
| jellifying agent | Xanthangum | | | | | | | 0.5 | | | |
| | Methylcellulose | | | | | | | | | | |
| | Hydroxypropylcellulose | | | | | | | | | | |
| Thickening/ | HydrophilicFumedSilica | 0.5 | 0.25 | 0.5 | 0 | 0.5 | | | 0.5 | 0.5 | 0.5 |
| Texturing agent | HydrophobicFumedSilica | | | | | | | | | | |
| | Acrylate or acrylamides polymers | 0.57 | 0.57 | 0.57 | 0.57 | 0.65 | 2 | 0.77 | 0.65 | 0.65 | 0.65 |
| | PVP | 1 | 0.5 | 1 | 0.5 | 1 | 1 | 1 | 1 | 1 | 1 |
| Set accelerator | Calcium chloride | | | | | | | | | | |
| | Calcium lactate | | | | | | | | | | |
| | Calcium carbonate | | | | | | | | | | |
| | Calcium oxide | | | | | | | | | | |

| | Components | Weight percentage (%) | | | | | | | | | |
|---|---|---|---|---|---|---|---|---|---|---|---|
| | C3S PHASE N° | 17 | 18 | 19 | 22 | 23 | 24 | 25 | 26 | 27 | 28 |
| Calcium silicate | C3S particles | 60 | 60 | 60 | 60 | 49.97 | 50 | 50 | 50 | 50 | 60 |
| | C2S particles | | | | | | | | | | |
| Radiopacifier | Zirconium oxide | 5.85 | 5.85 | 5.85 | 5.85 | 18.99 | 19.33 | 20.43 | 21.50 | 7.68 | 6.85 |
| | Bismuth oxide | | | | | | | | | | |
| | Barium sulfate | | | | | | | | | | |
| Non-aqueous | Caprylylmethicone | | | | 32 | | | | | | |
| carrier | Dimethicone | | 32 | | | 32 | | | | | |
| | Dipropylene glycol | 32 | | | | | | | | | |
| | Glycerol | | | | | | | | | | |
| | Propylene glycol | | | | | 26.98 | 27 | 27 | 27 | 27 | 32 |
| jellifying agent | Xanthangum | | | | | | | | | | |
| | Methylcellulose | | | | | 1 | | 1 | | | |
| | Hydroxypropylcellulose | | | | | | 0.5 | | 0.5 | | |
| Thickening/ | HydrophilicFumedSilica | 0.5 | 0.5 | 0.5 | 0.5 | 0.5 | 0.5 | 0.5 | 0.5 | 0.5 | 0.5 |
| Texturing agent | HydrophobicFumedSilica | | | | | | | | | | |
| | Acrylate or acrylamides polymers | 0.65 | 0.65 | 0.65 | 0.65 | 0.56 | 0.67 | 0.57 | | 0.57 | 0.65 |
| | PVP | 1 | 1 | 1 | 1 | | | | | | |
| Set accelerator | Calcium chloride | | | | | 2 | 2 | | | | |
| | Calcium lactate | | | | | | | 0.5 | 0.5 | | |
| | Calcium carbonate | | | | | | | | | 14 | |
| | Calcium oxide | | | | | | | | | 0.25 | |
| Surfactant | Polysorbate | | | | | | | | | | |

TABLE 1-continued

| Components | | Weight percentage (%) | | | | | | | | | |
|---|---|---|---|---|---|---|---|---|---|---|---|
| | C3S PHASE N° | 29 | 30 | 31 | 32 | 33 | 34 | 35 | 36 | 37 | 38 |
| Calcium silicate | C3S particles | 60 | 60 | 60 | 60 | 60 | 60 | 60 | 40 | | 20 |
| | C2S particles | | | | | | | | 10 | 50 | 30 |
| Radiopacifier | Zirconium oxide | | | | | | | | | | |
| | Bismuth oxide | 6 | 6 | 6 | 5.85 | | | 6 | 15.85 | 19 | 21.50 |
| | Barium sulfate | | | | | 5.85 | | | | | |
| Non-aqueous carrier | Caprylylmethicone | | | | | | 5.85 | | | | |
| | Dimethicone | | | | | | | | | | |
| | Dipropylene glycol | | | | | | | | | 1 | |
| | Glycerol | | | | | | | | | | |
| | Propylene glycol | 32 | 32 | 32 | 32 | 32 | 32 | 32 | 32 | 27 | 27 |
| jellifying agent | Xanthangum | | | | | | | | | | |
| | Methylcellulose | | 0.5 | | | | | | | | |
| | Hydroxypropylcellulose | | | 0.5 | | | | | | 0.5 | 0.5 |
| Thickening/ Texturing agent | HydrophilicFumedSilica | 0.5 | 0.5 | 0.5 | | 0.5 | 0.5 | 0.5 | 0.5 | 0.5 | 0.5 |
| | HydrophobicFumedSilica | | | | 0.5 | | | | | | |
| | Acrylate or acrylamides polymers | | | | 0.65 | 0.65 | 0.65 | | 0.65 | | 0.5 |
| | PVP | 1 | 1 | 1 | 1 | 1 | 1 | 1 | 1 | | |
| Set accelerator | Calcium chloride | | | | | | | | | 2 | |
| | Calcium lactate | | | | | | | | | | |
| | Calcium carbonate | | | | | | | | | | |
| | Calcium oxide | | | | | | | 0.5 | | | |
| Surfactant | Polysorbate | | 0.5 | | | | | 0.5 | | | |

TABLE 2

| | AQUEOUS PHASE N° | A | B | C | D | E | F | G | H | I |
|---|---|---|---|---|---|---|---|---|---|---|
| Set accelerator | Calcium chloride | 30 | 30 | 30 | 30 | 30 | 30 | 30 | 30 | 30 |
| Radiopacifier | Zirconium oxide | | 40 | 40 | 40 | 40 | 41 | 40.5 | 40 | 40 |
| | Barium sulfate | | | | | | | | | |
| | Bismuth oxide | | | | | | | | | |
| Carrier | Propylene glycol | | | | | | | | | |
| | Purified water | 59.5 | 25 | 17 | 18.5 | 26.5 | 26.5 | 26.5 | 26.5 | 26.5 |
| Water-reducing agents | Calcium silicates hydrates | 10 | | 10 | 10 | | | | | |
| | Hydrophilic copolymer | | 2 | | | 2 | 2 | 2 | 2 | 2 |
| | Vinylpolymer | 0.5 | | | | | | | | |
| jellifying agent | Hydroxyethyl cellulose | | 3 | 3 | 1.5 | 1.5 | 0.5 | 1 | | |
| | Methylcellulose | | | | | | | | | |
| | Acrylate or acrylamide polymers | | | | | | | | 1.5 | 1.5 |

| | AQUEOUS PHASE N° | J | K | M | N | O | P | Q | R | S |
|---|---|---|---|---|---|---|---|---|---|---|
| Set accelerator | Calcium chloride | 30 | 30 | 20 | 15 | 30 | 30 | 30 | 30 | 30 |
| Radiopacifier | Zirconium oxide | 33.4 | 34.5 | 40 | 36.45 | 34.5 | 36.5 | 34.5 | QS100* | QS100* |
| | Barium sulfate | | | | | | | | | |
| | Bismuth oxide | | | | | | | | | |
| Carrier | Propylene glycol | | | | 4 | | 4 | | | |
| | Purified water | 26.5 | 26.5 | 30 | 25 | 26.5 | 25 | 26.5 | 26.5 | 26.5 |
| Water-reducing agents | Calcium silicates hydrates | | | | | | | | | |
| | Hydrophilic copolymer | | | | | | | | | |
| | Vinylpolymer | | | | | | | | | |
| jellifying agent | Hydroxyethyl cellulose | | | | | | | | | |
| | Methylcellulose | | | | | | | | | 0.50 |
| | Acrylate or acrylamide polymers | 10.1 | 9 | | 4.55 | 9 | 4.55 | 9 | 0.65 | |

| | AQUEOUS PHASE N° | T | U | V | W | X | Y | Z | AA |
|---|---|---|---|---|---|---|---|---|---|
| Set accelerator | Calcium chloride | 20 | 15 | 30 | 30 | 30 | 30 | | 30 |
| Radiopacifier | Zirconium oxide | 44.5 | 49.5 | 37.45 | 38.45 | | | 73 | 33.5 |
| | Barium sulfate | | | | | | 34.5 | | |
| | Bismuth oxide | | | | | 34.5 | | | |

TABLE 2-continued

| Category | Component | | | | | | | | |
|---|---|---|---|---|---|---|---|---|---|
| Carrier | Propylene glycol | | | 3 | 2 | | | | |
| | Purified water | 26.5 | 26.5 | 25.0 | 25.0 | 26.5 | 26.5 | 26.5 | 26.5 |
| Water-reducing agents | Hydrophilic copolymer | | | | | | | | |
| | Vinylpolymer | | | | | | | | |
| jellifying agent | Hydroxyethyl cellulose | | | | | | | | |
| | Methylcellulose | | | | | | | | |
| | Acrylate or acrylamide polymers | 9 | 9 | 4.55 | 4.55 | 9 | 9 | 0.5 | 10 |

*added in the phase for complete formulation to 100%.

Part 2: Uses and Physico-Chemical Tests

Example 2: Injection System of the Invention

A double syringe was prepared with the kit of parts of the invention. In this aim, a double syringe was filled with 6 g of the anhydrous C3S phase in the first container and with 6 g of the aqueous phase in the second container. The mixture of the two pastes
(or semi-solids) is carried out in the mixing nozzle (see FIG. 1) in a volume ratio (C3S phase/aqueous phase) of about 1.

Several compositions can be obtained by mixing the anhydrous C3S phase and the aqueous phase as defined above. Especially, the composition 5K was prepared by mixing the anhydrous C3S phase N°5 and the aqueous phase K as defined above. Then, the mixture 5K was extruded by the double syringe and then tested as follows.

Appearance and Adhesion Ability

Figure 2:
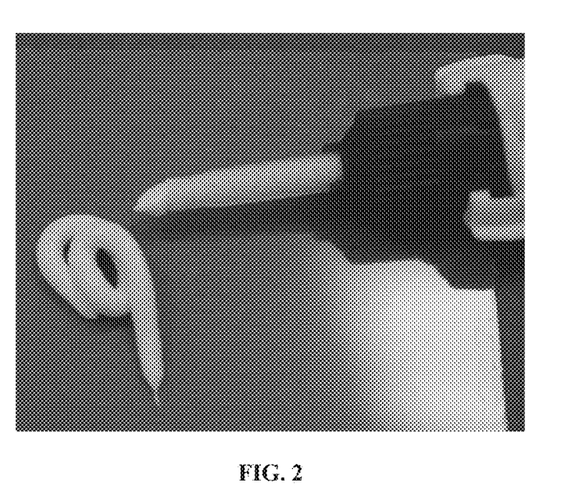
FIG. 2 is a photograph showing the white creamy mixture extruded from the injection system of the invention.

The composition 5K gives a white creamy composition (see FIG. 2). Furthermore, the composition 5K is consistent, slightly elastic, can be easily extruded from the double syringe and is able to adhere at Gutta Percha and/or to practitioner's tools.

Rheology

Figure 3:
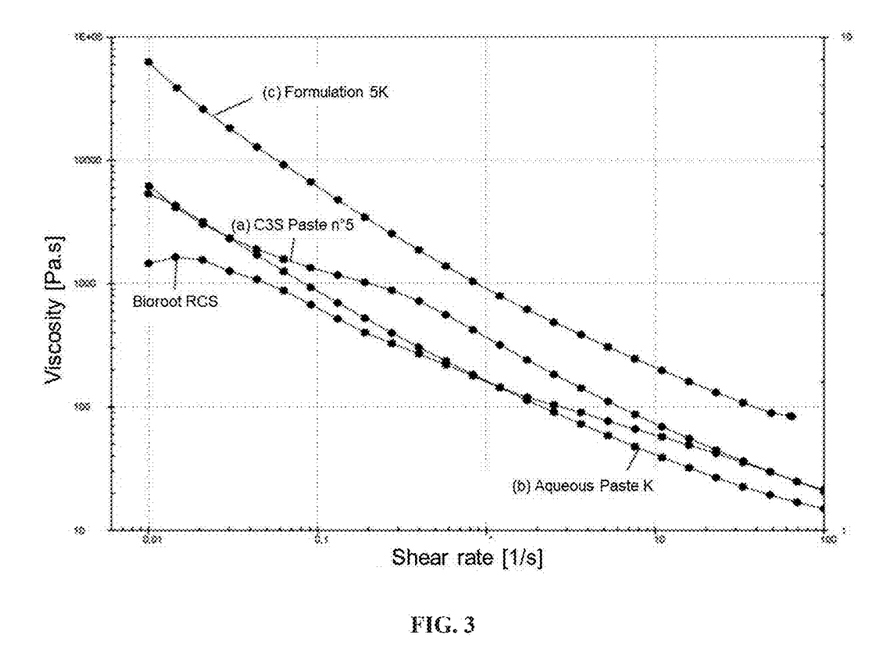
FIG. 3 is a graph showing the viscosity of different semi-solids: (a) the C3S semi-solid n°5, (b) the aqueous semi-solid K, (c) the resulting mixture 5K and a commercial dental composition BIOROOT RCS® depending on the shear gradient.

The rheological behavior of the composition 5K was carried out. The composition of the invention is a rheofluidifying composition (see FIG. 3).

Setting Time

The setting time for the composition 5K is about 3 hours.

Example 3: Injection System of the Invention Compared to an Injection System in which the Aqueous Paste of the Invention has been Replaced with an Aqueous Liquid Phase A double syringe A was prepared with the kit of parts of the invention. The double syringe A comprises:
  a first container, waterproof, filled with one of the anhydrous calcium silicate pastes as defined in Table 1; and
  a second container filled with one of the aqueous pastes as defined in Table 2;
  said calcium silicate paste and aqueous paste being in a volume ratio equals to 1.

A double syringe B was prepared as the double syringe A, except that the aqueous phase of the syringe A was replaced in the syringe B, by an aqueous liquid phase consisting of water, zirconium oxide and calcium chloride.

Two formulations of the aqueous liquid phase have been tested for syringe B:
  (b1) 30% water, 30% calcium chloride and 40% zirconium oxide (all the percentages are given by weight to the total weight of the aqueous liquid phase); and
  (b2) 46.9% water, 53.1% calcium chloride and no zirconium oxide (all the percentages are given by weight to the total weight of the aqueous liquid phase).

Each double syringe A or B has a nozzle for mixing the two phases contained in each compartment.

The dental materials extruded from each double syringe A and B, have been compared.

The composition extruded from the double syringe A (calcium silicate paste/aqueous paste) gives a white creamy composition which is homogenous, consistent, slightly elastic and that can be easily extruded from the double syringe A (same aspect as FIG. 2).

To the contrary, from the double syringe B (calcium silicate paste/aqueous liquid phase) it is not possible to mix the calcium silicate phase with the aqueous liquid phase. Whatever the formulation of the liquid phase b1 or b2, the water liquid phase is extracted from syringe B before the calcium silicate phase.

Figure 5:
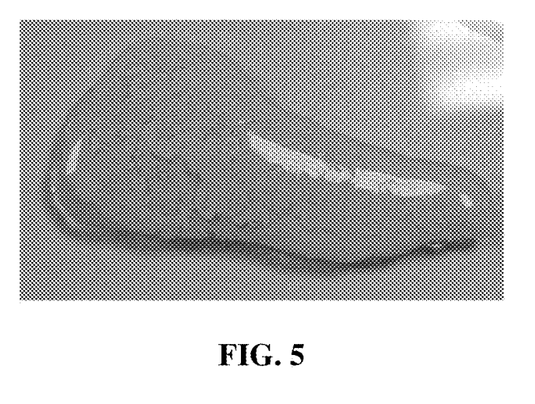
FIG. 5 is a photograph showing the heterogeneous mixture delivered from a double syringe having a first compartment filled with a calcium silicate paste and a second compartment filled with an aqueous liquid phase.

Thus, the resulting mixture of syringe B is strongly heterogeneous (see FIG. 5) and has not the desired consistency of a cream as searched. Consequently, a double syringe containing a calcium silicate paste and an aqueous liquid phase in a volume ratio equals to 1, does not provide any dental composition ready for use as those of the present invention.

Example 4: Injection System of the Invention Compared to a Commercially Available Product MTA Fillapex Manufactured by Angelus A double syringe A was prepared with the kit of parts of the invention.

The use of the double syringe A and the properties of the dental material obtained from the syringe A, have been compared to an endodontic sealer (based on resin materials) which is commercially available under the form of a double syringe, the product MTA Fillapex manufactured by Angelus.

Extractive Strength

First, the strength to be applied on each syringe for delivering the composition mixed in situ in the nozzle, was determined.

For this goal, the measurement is performed on 3 filled syringes equipped with an endodontic tip. Extractive strength is measured on a MTS Bench.

The average extractive strength for the double syringe A with the kit of parts of the invention is 22 N compared to 60 N for MTA Fillapex.

Figure 6:
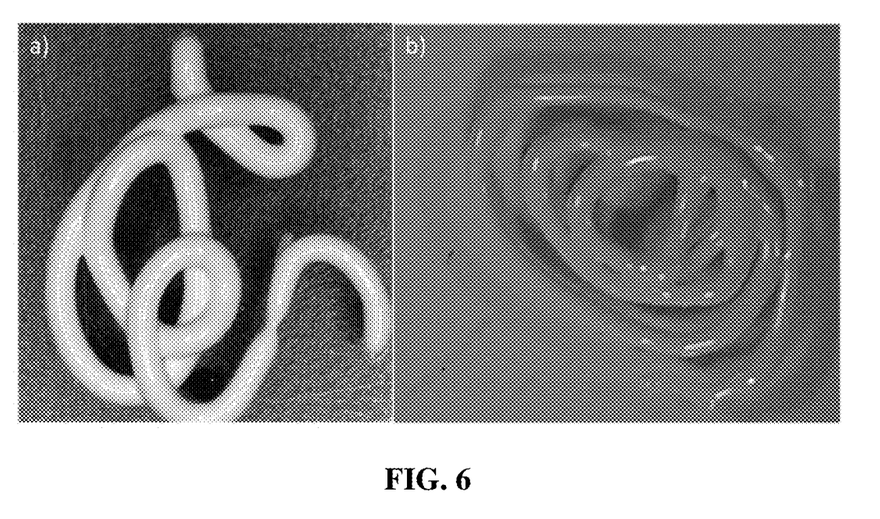
FIG. 6 is a set of photographs showing the homogenous and creamy composition delivered by the double syringe of the invention (6a) and the composition delivered by the MTA Fillapex double syringe (6b).

Furthermore, it is observed that the dental composition obtained from the syringe A has a better consistency for being used by the practitioner (see FIG. 6a) than those of MTA Fillapex (FIG. 6b).

In conclusion, it is easier for the practitioner to use the double syringe of the invention compared to MTA Fillapex and the resulting dental composition of the invention has a better consistency for dental filling.

Compressive Strength

Secondly, the compressive strength for each dental material extruded from the syringe A or MTA Fillapex was determined.

For this goal, the dental material of each syringe is dispensed in a mold (6 mm height, 4 mm of diameter). 7 specimens are prepared and allowed to set at 37° C. and 100% relative humidity in a water bath for 48 h. Then, the specimens are polished and unmolded.

Measurement is performed using the MTS Bench in the method as described herein before.

The resulting average compressive strength (at 48 h) is 9.25 MPa for the double syringe A with the kit of parts of the invention. To the contrary, at 48 h, the dental material obtained from MTA Fillapex is still soft so that it is not possible to obtain any compressive strength values.

In conclusion, the double syringe A comprising the kit of parts of the invention, provides a dental material able to quickly hardens compared to the product MTA Fillapex.

The product MTA Fillapex does not comprise any water and the hardening of the product MTA Fillapex depends on the amount of water brought by the patient's tissues.

Without to be bound by any theory, the fast hardening of the dental material of the invention results from the hydration of the calcium silicate paste when mixing it with the aqueous paste in the nozzle of the double syringe A. Thus, the hardening of the dental material of the invention only depends on the amount of water provided by the aqueous paste but not of the amount of water brought by the patient's tissues.

pH

Thirdly, the pH of the environment induced in situ by each dental material extruded from the syringe A or MTA Fillapex was measured at the extrusion time (t0), after 2 h and after 24 h.

For this aim, the extruded dental material is placed into a mold. Then, the molded dental material is immersed in a beaker containing 20 mL of purified water. The pH is measured at t0, after 2 h and after 24 h.

Each pH measurement is carried out three times. The results are presented in the following Table:

|  | From the dental product of the invention | From the dental product of MTA Fillapex |
| --- | --- | --- |
| Average pH à t0 | 7.1 | 6.2 |
| Average pH after 2 h | 10.5 | 8.6 |
| Average pH after 24 h | 11.8 | 9.3 |

These results show that the pH of the environment surrounding the dental material of the invention, is more alkaline than those of MTA Fillapex.

Consequently, the pH of the environment induced by the dental materials of the invention contributes to avoid the bacterial proliferation in situ.

Apical Sealing

Finally, the apical sealing for each dental material extruded from the syringe A or MTA Fillapex was determined after 8 days.

For this aim, 3 specimens for each dental material have been prepared according to the following method:

3 pipette cones are cutted to 2 cm and filled with the sample to be tested so as not to create a bubble; and then gutta percha points are added leaving about 2 mm of the apical side (side of the smaller diameter cone) The excess of sample is leveled off;

The 3 samples are placed in a test tube filled with purified water and the caps are closed;

The samples are immerged into a water bath maintained at 37° C. for 7 days.

After 7 days, the purified water is replaced by a 0.04% solution of methylene blue. The cap of the tube is replaced and the samples are again placed in a water bath at 37° C. for 24 h. This dye is used as its low molecular weight enables it to penetrate more deeply than the other dyes along the root canal.

Then, the samples are washed with purified water, dried and observed by microscope (Keyence) and the infiltration length of the methylene blue solution, is measured.

Samples are then molded in an acrylic resin (Metafix, Struers) in order to facilitate the cutting of the tooth in the main root axis, with the Struers Accutom. Dye penetration is observed by a Keyence microscope.

The results show that from the dental material of the invention, the average apical sealing after 8 days, is 1.5 mm whereas from MTA Fillapex, the average apical sealing is 2.3 mm.

In conclusion, the double syringe A of the invention provides a dental material having good apical sealing.

The invention claimed is:

1. A kit of parts for providing a calcium-silicate based cement, said kit of parts comprising a first container and a second container, wherein:
   the first container is waterproof and comprises a anhydrous calcium silicate semi-solid comprising calcium silicate particles and a non-aqueous carrier;
   the second container comprises an aqueous semi-solid comprising purified water, a radiopacifier, and a set accelerator;
   the volume ratio between the anhydrous calcium silicate semi-solid and the aqueous semi-solid ranges from 1 to 10;
provided that said first and second containers do not comprise any phosphorus compounds.

2. The kit of parts according to claim 1, wherein the non-aqueous carrier is selected from glycol compounds and/or silicones and mixtures thereof.

3. The kit of parts according to claim 1, wherein the size of calcium silicate particles ranges from 0.01 μm to 50 μm.

4. The kit of parts according to claim 1, wherein the radiopacifier is selected from the group consisting of bismuth oxide, strontium carbonate, barium sulfate, tantalum oxide, cerium oxide, tin oxide, zirconium oxide compounds and radiopaque glasses containing tantalum, barium and strontium, and mixtures thereof.

5. The kit of parts according to claim 1, wherein the set accelerator is selected from the group consisting of calcium carbonate, calcium oxide, sodium bicarbonate, calcium lactate, calcium chloride and mixtures thereof.

6. The kit of parts according to claim 1, wherein the calcium silicate semi-solid and/or the aqueous semi-solid further comprises additives.

7. The kit of parts according to claim 1, wherein the first container comprises a calcium silicate semi-solid consisting of:
   from 50 to 90% of tricalcium silicate particles,
   from 10 to 50% of non-aqueous carrier,
   from 0% to 25% of a radiopacifier, and
   from 0% to 5% of additives; by weight to the total weight of the calcium silicate semi-solid; and wherein the second container comprises an aqueous semi-solid consisting of:
from 10 to 50% of purified water,
from 10 to 75% of a set accelerator,
from 10% to 80% of a radiopacifier, and
from 0% to 20% of additives; by weight to the total weight of the aqueous semi-solid.

8. The kit of parts according to claim 1, wherein the first container comprises a anhydrous calcium silicate semi-solid consisting of tricalcium silicate particles and propylene glycol; and the second container comprises an aqueous semi-solid consisting of purified water, calcium chloride, zirconium oxide and additives.

9. A delivery system for delivering a self-hardening calcium-silicate based cement, said system comprising the kit of parts according to claim 1 and a mixing chamber.

10. The delivery system of claim 9, further comprising a plunger.

11. The delivery system of claim 9, wherein the non-aqueous carrier is selected from glycol compounds and/or silicones and mixtures thereof.

12. The delivery system of claim 9, wherein the size of calcium silicate particles ranges from 0.01 μm to 50 μm.

13. The delivery system of claim 9, wherein the radiopacifier is selected from the group consisting of bismuth oxide, strontium carbonate, barium sulfate, tantalum oxide, cerium oxide, tin oxide, zirconium oxide compounds and radiopaque glasses containing tantalum, barium and strontium, and mixtures thereof.

14. The delivery system of claim 9, wherein the set accelerator is selected from the group consisting of calcium carbonate, calcium oxide, sodium bicarbonate, calcium lactate, calcium chloride and mixtures thereof.

15. The delivery system of claim 9, wherein the calcium silicate semi-solid and/or the aqueous semi-solid further comprises additives.

16. The delivery system of claim 9, wherein the first container comprises a calcium silicate semi-solid consisting of:
from 50 to 90% of tricalcium silicate particles,
from 10 to 50% of non-aqueous carrier,
from 0% to 25% of a radiopacifier, and
from 0% to 5% of additives; by weight to the total weight of the calcium silicate semi-solid; and
wherein the second container comprises an aqueous semi-solid consisting of:
from 10 to 50% of purified water,
from 10 to 75% of a set accelerator,
from 10% to 80% of a radiopacifier, and
from 0% to 20% of additives; by weight to the total weight of the aqueous semi-solid.

17. The delivery system of claim 9, wherein the first container comprises a anhydrous calcium silicate semi-solid consisting of tricalcium silicate particles and propylene glycol; and the second container comprises an aqueous semi-solid consisting of purified water, calcium chloride, zirconium oxide and additives.

\* \* \* \* \*